United States Patent [19]
Gildert et al.

[11] Patent Number: 5,877,363
[45] Date of Patent: Mar. 2, 1999

[54] PROCESS FOR CONCURRENT SELECTIVE HYDROGENATION OF ACETYLENES AND 1,2 BUTADINE IN HYDROCARBON STREAMS

[75] Inventors: Gary R. Gildert; Hugh M. Putman, both of Houston; Dennis Hearn, Seabrook, all of Tex.

[73] Assignee: Catalytic Distillation Technologies, Pasadena, Tex.

[21] Appl. No.: 717,934

[22] Filed: Sep. 23, 1996

[51] Int. Cl.$^6$ .............................. C07C 5/08; B01D 3/34
[52] U.S. Cl. ..................... 585/260; 585/259; 585/275; 585/277; 585/841; 203/29; 203/32; 203/DIG. 6
[58] Field of Search .................... 585/324, 259, 585/260, 275, 277, 841; 526/77; 203/28, 29, 32, DIG. 6

[56] References Cited

U.S. PATENT DOCUMENTS

| | | | |
|---|---|---|---|
| 2,493,499 | 1/1950 | Perry | 585/253 |
| 2,717,202 | 9/1955 | Bailey | 23/283 |
| 3,186,935 | 6/1965 | Vaell | 208/59 |
| 3,531,542 | 9/1970 | Myers et al. | 260/683.2 |
| 3,839,486 | 10/1974 | Arganbright | 260/683.2 |
| 4,213,847 | 7/1980 | Chen et al. | 208/111 |
| 4,215,011 | 7/1980 | Smith, Jr. | 252/426 |
| 4,221,653 | 9/1980 | Chervenak et al. | 208/8 |
| 4,232,177 | 11/1980 | Smith, Jr. | 585/324 |
| 4,242,530 | 12/1980 | Smith, Jr. | 585/510 |
| 4,293,728 | 10/1981 | Montgomery | 585/670 |
| 4,302,356 | 11/1981 | Smith, Jr. | 252/426 |
| 4,307,254 | 12/1981 | Smith, Jr. | 568/697 |
| 4,336,407 | 6/1982 | Smith, Jr. | 568/697 |
| 4,361,422 | 11/1982 | Derrien et al. | 44/56 |
| 4,361,713 | 11/1982 | Kaeding | 585/467 |
| 4,396,790 | 8/1983 | Ward | 585/664 |
| 4,404,124 | 9/1983 | Johnson et al. | 252/466 |
| 4,417,089 | 11/1983 | Drake | 585/670 |
| 4,439,350 | 3/1984 | Jones, Jr. | 502/527 |
| 4,443,559 | 4/1984 | Smith, Jr. | 502/527 |
| 4,482,775 | 11/1984 | Smith, Jr. | 585/671 |
| 4,504,687 | 3/1985 | Jones, Jr. | 568/697 |
| 4,533,779 | 8/1985 | Boitiaux et al. | 585/259 |
| 4,536,373 | 8/1985 | Jones, Jr. | 422/211 |
| 4,721,827 | 1/1988 | Cullo et al. | 585/467 |
| 4,724,274 | 2/1988 | Boitiaux et al. | 585/668 |
| 4,740,633 | 4/1988 | Boitaux et al. | 568/699 |
| 4,761,514 | 8/1988 | Menard | 585/475 |
| 4,849,569 | 7/1989 | Smith, Jr. | 585/466 |
| 5,012,021 | 4/1991 | Vora et al. | 585/315 |
| 5,030,786 | 7/1991 | Shamshoum et al. | 585/467 |
| 5,087,780 | 2/1992 | Arganbright | 585/259 |
| 5,240,892 | 8/1993 | Klocke | 502/77 |
| 5,281,753 | 1/1994 | Olson et al. | 585/260 |
| 5,321,163 | 6/1994 | Hickey et al. | 568/59 |
| 5,431,888 | 7/1995 | Hickey et al. | 422/191 |
| 5,464,799 | 11/1995 | Casci et al. | 502/65 |
| 5,476,978 | 12/1995 | Smith, Jr. et al. | 585/323 |

FOREIGN PATENT DOCUMENTS

| | | |
|---|---|---|
| 0087980 | 7/1983 | European Pat. Off. . |
| 835689 | 5/1960 | United Kingdom . |
| 920012 | 3/1963 | United Kingdom . |

OTHER PUBLICATIONS

Buselli. Butene–1 to polybutylene–economic outlook & prospects. Amer. Chemical Society. Mar. 1978, p. 808.

Heck, et al., Catalytic Process Using C4 Streams for Octane Improvement: Hydro–ISO. & MTBE. Amer. Chem. Society. Mar. 1980, pp. 38–50.

Boitaux et al., Newest Hydrogen Catalysts. Hydrocarbon Processing. Mar. 1985, pp. 51–59.

*Primary Examiner*—Fred Teskin
*Attorney, Agent, or Firm*—Kenneth H. Johnson

[57] ABSTRACT

A process for the removal of vinylacetylene, ethylacetylene and 1,2-butadiene from $C_4$ aliphatic hydrocarbon streams comprising, concurrently: (1) feeding hydrogen and a hydrocarbon stream comprising $C_4$ hydrocarbons including butanes, butenes, butadienes and vinylacetylene to a distillation column reactor containing a bed comprising a hydrogenation catalyst of the type characterized by platinum, palladium or rhodium which is prepared as a distillation structure to selectively hydrogenate a portion of the vinylacetylene and the 1,2-butadiene and (2) fractionally distilling the reaction mixture to remove a heavier fraction and removing a fraction overhead comprising substantially all of the $C_4$.

17 Claims, 1 Drawing Sheet

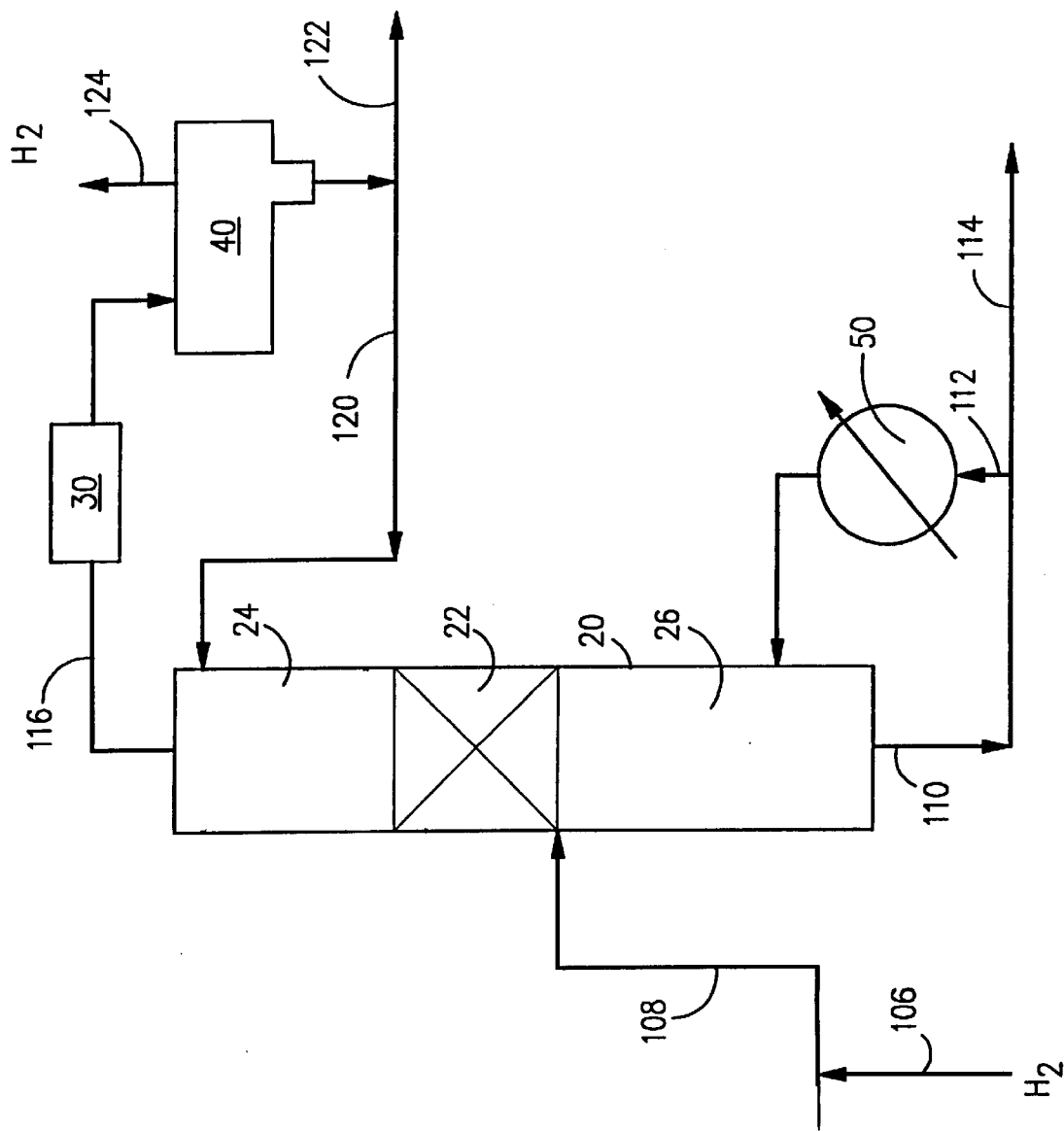

PROCESS FOR CONCURRENT SELECTIVE HYDROGENATION OF ACETYLENES AND 1,2 BUTADINE IN HYDROCARBON STREAMS

BACKGROUND OF THE INVENTION

1. Field of the Invention

The present invention relates to the concurrent selective hydrogenation of vinylacetylene, ethylacetylene and 1,2-butadiene in an olefin rich $C_4$ stream. More particularly the invention relates to a process utilizing hydrogenation catalysts in a structure to serve as both the catalyst and as a distillation structure for the simultaneous reaction and separation of the reactants and reaction products.

2. Related Information

Petroleum distillate streams contain a variety of organic chemical components. Generally the streams are defined by their boiling ranges which determine the compositions. The processing of the streams also affects the composition. For instance, products from either catalytic cracking or thermal cracking processes contain high concentrations of olefinic materials as well as saturated (alkanes) materials and poly-unsaturated materials (diolefins). Additionally, these components may be any of the various isomers of the compounds.

Refinery streams contain a broad spectrum of olefinic compounds. This is especially true of products from either catalytic cracking or thermal cracking processes. These unsaturated compounds comprise ethylene, acetylene, propylene, propadiene, methyl acetylene, butenes, butadiene, amylenes, hexenes etc. Many of these compounds are valuable, especially as feed stocks for chemical products. Ethylene, especially is recovered. Additionally, propylene and the butenes are valuable. However, the olefins having more than one double bond and the acetylenic compounds (having a triple bond) have lesser uses and are detrimental to many of the chemical processes in which the single double bond compounds are used, for example, polymerization. Over the range of hydrocarbons under consideration, the removal of highly unsaturated compounds is of value as a feed pretreatment since these compounds have frequently been found to be detrimental in most processing, storage and use of the streams.

Boitiaux, et al in "Newest Hydrogenation Catalyst", *Hydrocarbon Processing*, March 1985, p. 51–59, present an overview of various uses of hydrogenation catalysts, including selective hydrogenation, utilizing a proprietary bimetallic hydrogenation catalyst. More particularly at page 56, the authors show that the only significant transformation of components is vinylacetylene to 1,3-butadiene with the improved catalysts in a stream also containing 1-butyne, 1,2-butadiene and olefins.

U.S. Pat. No. 4,067,921 discloses a process known as the Dow K Process, where acetylenes are hydrogenated in a diene stream containing principally 1,3-butadiene and trace amounts of vinylacetylene, ethylacetylene, and 1,2-butadiene, with substantial elimination of vinylacetylene with a small loss of 1,3-butadiene, but substantially no reduction in 1,2-butadiene (Table IV).

It is an advantage of the present invention that reduction of vinylacetylene, ethylacetylene and 1,2-butadiene is obtained in $C_4$ olefin containing streams. It is a particular advantage that this may be achieved in a single reactive distillation column by using beds of function specific catalyst.

SUMMARY OF THE INVENTION

The present invention presents a process for the removal of acetylenes and/or 1,2-butadiene from $C_4$ aliphatic hydrocarbon streams comprising concurrently:

(1) feeding hydrogen and a hydrocarbon stream comprising $C_4$ hydrocarbons including butanes, butenes, 1-3-butadiene, 1,2-butadiene and acetylenes to a distillation column reactor containing a bed comprising a hydrogenation catalyst of the type characterized by platinum, palladium or rhodium, preferably selected from platinum, palladium, rhodium or mixtures thereof, and prepared as a distillation structure under hydrogenation conditions to selectively hydrogenate a portion of the acetylenes and 1,2-butadiene to form a reaction mixture and (2) fractionally distilling the reaction mixture to remove a heavier fraction and removing a fraction overhead comprising substantially all of the $C_4$ compounds having reduced acetylenes and 1,2-butadiene content.

The hydrogenation of the more highly unsaturated compounds will produce more mono-olefins and/or alkanes. Also there may be bond shifting isomerization such as butene-2 to butene-1.

Generally the catalytic material in the bed is initially present as the metal oxide and may be converted to the hydride form during use by the hydrogen.

In the present invention hydrogen is provided at an effectuating hydrogen partial pressure of at least about 0.1 psia to and 75 psia, preferably less than 70 psia, preferably less than 50 psia, more preferably less than 35 psia to the distillation column reactor containing hydrogenation catalysts as described.

BRIEF DESCRIPTION OF THE DRAWING

The FIGURE is a flow diagram in schematic form of a preferred embodiment of the invention.

DESCRIPTION OF THE PREFERRED EMBODIMENTS

The present invention provides a process for selectively hydrogenating diolefins and particularly acetylenes and isomerizing the mono-olefins toward equilibrium.

In the usual application of a process where the catalyst serves as a distillation component, the equilibrium is constantly disturbed, thus driving the reaction toward completion, that is, the reaction has an increased driving force because the reaction products have been removed and cannot contribute to a reverse reaction (LeChatelier's Principle). Although the hydrogenation reactions have been described as reversible at elevated temperatures above about 900° F., under the temperature conditions employed in the present invention, the hydrogenation is not reversible and cannot be an incentive to use a catalytic distillation system. The poor performance of prior vapor phase hydrogenations would not suggest the use of distillation type reaction. In particular the prior art would not suggest that the undesirable 1,2-butadiene and the acetylenes specifically vinyl acetylene and ethylacetylene could both be substantially reduced in the $C_4$ product overhead.

It is believed that in the present reaction catalytic distillation is a benefit first, because the reaction is occurring concurrently with distillation, and the initial reaction products and other stream components are removed from the reaction zone as quickly as possible reducing the likelihood of side reactions. Second, because all the components are boiling the temperature of reaction is controlled by the boiling point of the mixture at the system pressure. The heat of reaction simply creates more boil up but no increase in temperature at a given pressure. As a result, a great deal of control over the rate of reaction and distribution of products can be achieved by regulating the system pressure. Also, adjusting the throughput (residence time=liquid hourly space velocity$^{-1}$) gives further control of product distribution and to a degree control of the side reactions such as oligomerization. A further benefit that this reaction may gain from catalytic distillation is the washing effect that the internal reflux provides to the catalyst thereby reducing polymer build up and coking. Internal reflux may be varied over the range of 0.1 to 40 preferably 0.2 to 20 L/D (wt. liquid just below the catalyst bed/wt. distillate) and gives excellent results, and with the $C_3$–$C_5$ streams being usually in the range of 0.5 to 4.0 L/D.

Quite surprisingly the low hydrogen partial pressure used in the distillation system did not result in the failure of the hydrogenation which would have been expected based on the high hydrogen partial pressure found in the liquid phase systems which are the worldwide standard. Without limiting the scope of the invention it is proposed that the mechanism that produces the effectiveness of the present process is the condensation of a portion of the vapors in the reaction system, which occludes sufficient hydrogen in the condensed liquid to obtain the requisite intimate contact between the hydrogen and the highly unsaturated compounds in the presence of the catalyst to result in their hydrogenation. This phenomenon of condensation which is a constant factor in a distillation is believed to result in the same or better hydrogen availability, as the high pressure in the liquid phase, that is, the hydrogen is introduced into the liquid so that the hydrogenation occurs.

The $C_4$'s in the feed to the present unit are contained in a single cut which may contain everything from $C_2$'s through $C_5$'s and higher. Mixed refinery streams often contain a broad spectrum of olefinic compounds. This is especially true of products from either catalytic cracking or thermal cracking processes. Refinery streams are usually separated by fractional distillation, and because they often contain compounds that are very close in boiling points, such separations are not precise. A $C_5$ stream, for instance, may contain $C_3$'s and up to $C_8$'s.

Catalysts which are useful in all the reactions include the Group VIII metals. The preferred catalyst for the selective hydrogenation and isomerization is palladium. The catalyst may be used as individual Group VIII metal components or in admixture with each other or modifiers as known in the art, particularly those in Group VIB and IB.

Generally the metals are deposited as the oxides on an alumina support. The supports are usually small diameter extrudates or spheres, typically alumina. The catalyst must then be prepared in the form of a catalytic distillation structure. The catalytic distillation structure must be able to function as catalyst and as mass transfer medium. The catalyst must be suitably supported and spaced within the column to act as a catalytic distillation structure. In a preferred embodiment the catalyst is contained in a woven wire mesh structure as disclosed in U.S. Pat. No. 5,266,546 which is hereby incorporated by reference. Other catalytic distillation structures useful for this purpose are disclosed in U.S. Pat. Nos. 4,731,229, 5,073,236 and 5,431,890 which are also incorporated by reference.

The catalytic distillation bed contains a supported palladium catalytic distillation structure which selectively hydrogenates the 1,2-diolefins and acetylenes.

Hydrogen is provided as necessary to support the reaction. The distillation column reactor may be operated at a pressure such that the reaction mixture is boiling in the bed of catalyst. A "froth level", as described in U.S. Pat. No. 5,221,441 which is incorporated herein, may be maintained throughout the catalyst bed by control of the bottoms and/or overheads withdrawal rate, although the preferred operation is without the froth.

The present process preferably operates at overhead pressure of said distillation column reactor in the range between 0 and 250 psig and temperatures within said distillation reaction zone in the range of 60° to 300° F., preferably 100° to 170° F.

The feed and the hydrogen are preferably fed to the distillation column reactor separately or they may be mixed prior to feeding. A mixed feed is fed below the catalyst bed or at the lower end of the bed. Hydrogen alone is fed below the catalyst bed and the hydrocarbon stream is fed below the bed to about the mid one-third of the bed. The pressure selected is that which maintains catalyst bed temperature between 100° F. and 300° F.

A preferred catalyst for the selective hydrogenation/isomerization reactions is palladium oxide, preferably 0.1 to 5.0 weight %, supported on an appropriate support medium such as alumina, carbon or silica, e.g., ⅛" alumina extrudates. The catalyst used is 0.5 wt % Pd on ⅛" $Al_2O_3$ (alumina) extrudates, hydrogenation catalyst, supplied by Calsicat designated as E144SDU. Typical physical and chemical properties of the catalyst as provided by the manufacturer are as follows:

TABLE I

| Designation | E144SDU |
| --- | --- |
| Form | spheres |
| Nominal size | 8 × 14 Mesh |
| Pd. wt % | 0.5 |
| Support | High purity alumina |

The hydrogen rate to the distillation column reactor must be sufficient to maintain the reaction, but kept below that which would cause flooding of the column which is understood to be the "effectuating amount of hydrogen" as that term is used herein. Generally the mole ratio of hydrogen to 1,2-butadiene and acetylenes in the feed is at least 1.0 to 1.0, preferably at least 2.0 to 1.0 and more preferably at least 10 to 1.0.

Nickel catalyst also catalyzes the selective hydrogenation of the 1,2-butadiene and acetylenes. However, the palladium catalyst is preferred for these reactions. Generally the relative absorption preference is as follows:

(1) acetylenes
(2) diolefins
(3) mono-olefins

If the catalyst sites are occupied by a more strongly absorbed species, reaction of these weaker absorbed species cannot occur.

The reactions of the $C_4$'s of interest are:

(1) acetylenes+hydrogen to butanes and butenes; and
(2) butadiene-1,2+hydrogen to butene-1 and butene-2;

The present invention carries out the method in a catalyst packed column which can be appreciated to contain a vapor phase and some liquid phase as in any distillation. The distillation column reactor is operated at a pressure such that the reaction mixture is boiling in the bed of catalyst. The present process operates at overhead pressure of said distillation column reactor in the range between 0 and 350 psig, preferably 250 or less and temperatures within said distillation reaction zone in the range of 40° to 300° F., preferably 110° to 270° F. at the requisite hydrogen partial pressures. The feed weight hourly space velocity (WHSV), which is herein understood to mean the unit weight of feed per hour entering the reaction distillation column per unit weight of catalyst in the catalytic distillation structures, may vary over a very wide range within the other condition perimeters, e.g. 0.5 to 35.

The advantages of utilizing a distillation column reactor in the instant selective hydrogenation process lie in the better selectivity for the conversion of 1,2-diene and acetylene, conservation of heat and the separation by distillation which can remove some undesirable compounds, e.g. the heavies, TBC and $C_5$'s and the distillation can concentrate desired components in the catalyst zone.

The temperature in the distillation column reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus effected by a change in pressure; by increasing the pressure, the temperature in the system is increased, and vice versa.

Referring now to the FIGURE there is depicted a simplified flow diagram of one embodiment of the invention. The $C_4$ feed 108 is combined with hydrogen from flow line 106 and fed to the distillation column reactor 20.

Distillation column reactor 20 is shown to have a stripping section 26 in the lower half and a rectifying section 24 in the upper half. The catalyst bed is disposed in the rectifying section. The catalyst bed 22 contains the palladium oxide in the form of a catalytic distillation structure for the selective hydrogenation/isomerization reactions.

The combined feed stream in flow line 108 is fed into the distillation column reactor directly below the bed 22. The $C_5$+ material is separated from the $C_4$ and lighter material in the stripping section 26 with the $C_4$ and lighter material boiling up into the catalyst bed. The $C_5$+ heavier material exits via flow line 110. A portion of the bottoms may be circulated through reboiler 50 via flow line 112 to provide heat balance to the column. The remainder of the bottoms are taken via flow line 114.

The $C_4$ and lighter material is then boiled upward into the upper bed 24 of the rectifying section where the material is contacted with hydrogen in the presence of the palladium catalyst. A portion of diolefins and acetylenes are selectively hydrogenated to mono-olefins and the mono-olefins are isomerized toward equilibrium.

The $C_4$ and lighter distillate ($C_4$—), with reduced 1,2diolefins and acetylenes is removed as overheads via flow line 116 and passed through condenser 30 where the condensible materials are condensed. The liquids are collected in accumulator 40 where the gaseous materials, including any unreacted hydrogen, are separated and removed via flow line 124. The unreacted hydrogen may be recycled (not shown) if desired. The liquid distillate product is removed via flow line 122. Some of the liquid is recycled to the column 20 as reflux via line 120.

Generally the butadiene is separated from the remainder of the $C_4$ and lighter material and the $C_4$ olefin stream may be used as feed stock for a polymerization plant where it is converted to synthetic rubber, latex, etc.

EXAMPLE 1

In the Examples a one inch diameter column is loaded with 10 feet of the palladium catalyst as distillation structure in the upper portion of the column. A stripping section of 2 feet containing Pall rings was left below the catalyst bed.

The feed to the reaction distillation column was a $C_4$ cut. The analyses, conditions and results are shown in TABLE II below. The chromatographic analysis of the overheads was conducted for undesirables.

TABLE II

| Conditions | | | | | |
|---|---|---|---|---|---|
| hours | | | 47 | | |
| Pressure, psig | | | 58 | | |
| H₂ partial press. psia | | | 1.1 | | |
| Temperature, °F. | | | | | |
| ovhd | | | 110 | | |
| bed | | | ≈115 | | |
| btms | | | 124 | | |
| Flow rates, lbs/hr | | | | | |
| feed | | | 1 | | |
| ovhd | | | 0.9 | | |
| btms | | | 0.1 | | |
| H₂ rate, scfh | | | 0.3 | | |
| COMPONENT | FEED | H2 | OVERHEAD | BOTTOMS | % CHANGE |
| Analysis | | | | | |
| HOURS | 47.0 | | 47.0 | 41.0 | |
| $H_2$ | | 100.00% | | | |
| $N_2$ | | | | | |
| $C_2=$ | 0.01% | | 0.00% | 0.00% | |
| $C_2$ | 0.04% | | 0.00% | 0.00% | |
| $C_3=$ | 0.11% | | 0.07% | 0.00% | −45% |
| $C_3$ | 0.18% | | 0.07% | 0.01% | −66% |
| MeAcet | 0.15% | | 0.07% | 0.02% | −57% |
| Propadiene | 0.05% | | 0.02% | 0.01% | −60% |
| Cyclo $C_3$ | 0.02% | | 0.01% | 0.00% | −43% |
| $iC_4$ | 1.79% | | 1.54% | 0.78% | −18% |
| iB= | 11.77% | | 11.64% | 9.38% | −3% |
| 1-B= | 11.69% | | 13.91% | 9.86% | −16% |
| 1,3-BD | 58.87% | | 57.16% | 56.01% | −3% |
| $nC_4$ | 5.42% | | 5.46% | 5.45% | 1% |
| ViAcet | 1.887% | | .4985% | 1.9251% | −66% |
| trans 2-B= | 3.44% | | 5.14% | 6.06% | 53% |
| EtAcet | .6314% | | .2810% | .4505% | −53% |
| MeCyc $C_3$ | 0.03% | | 0.03% | 0.03% | 5% |
| cis 2-B= | 3.33% | | 3.82% | 6.05% | 21.% |
| 1,2-BD | 0.22% | | 0.10% | 0.63% | −32.% |
| $C_5$'s | 0.26% | | 0.03% | 2.07% | −13% |
| HVY's | 0.10% | | 0.13% | 0.94% | 109% |
| Total | 100.00% | | 00.00% | 100.00% | 0.00% |
| lb/hr | 1.0 | .0017 | 0.9 | 0.1 | |

EXAMPLE 2

Substantially the same results were obtained using the process on similar feeds with a similar catalyst in a three inch column, but over 99% of the $C_4$'s were recovered overhead.

The invention claimed is:

1. A process for the removal of acetylenes and 1,2-butadiene from $C_4$ aliphatic hydrocarbon streams comprising:

(a) feeding hydrogen and a $C_4$ hydrocarbon stream comprising 1,2-butadiene and acetylenes to a distillation column reactor containing a bed of hydrogenation catalyst selected from platinum, palladium, rhodium or mixtures thereof; (b) concurrently in said distillation column reactor;

(1) contacting said hydrocarbon stream and hydrogen in the presence of said hydrogenation catalyst under hydrogenation conditions to selectively hydrogenate a portion of the acetylenes and the 1,2-butadiene to form a reaction mixture, and (2) fractionally distilling the reaction mixture to remove a heavier fraction and removing a fraction overhead comprising substantially all of the $C_4$ compounds having reduced acetylenes and 1,2-butadiene content.

2. The process according to claim 1 wherein said hydrogenation catalyst is selected from platinum, palladium or rhodium.

3. The process according to claim 1 wherein the pressure within said distillation column reactor is between 0 and 350 psig.

4. The process according to claim 1 wherein the hydrogen partial pressure within said distillation column reactor is less than 50 psia.

5. The process according to claim 4 wherein the hydrogen partial pressure within said distillation column reactor is less than 35 psia.

6. The process according to claim 1 wherein said acetylenes comprise vinylacetylenes.

7. The process according to claim 1 wherein said acetylenes comprise ethylacetylenes.

8. The process according to claim 1 wherein said catalyst is platinum.

9. The process according to claim 1 wherein the L/D ratio of the internal reflux of the fractional distillation is in the range of 0.1 to 40.

10. The process according to claim 9 wherein the L/D is in the range of 0.5 to 4.0.

11. A process for the removal of acetylenes and 1,2-butadiene from $C_4$ aliphatic hydrocarbon streams comprising:

(a) feeding hydrogen and a $C_4$ hydrocarbon stream comprising 1,2-butadiene and acetylenes to a distillation column reactor containing a bed of platinum hydrogenation catalyst prepared as a distillation structure; (b) concurrently in said distillation column reactor;

(1) contacting said hydrocarbon stream and hydrogen in the presence of said hydrogenation catalyst under hydrogenation conditions to selectively hydrogenate a portion of the acetylenes and the 1,2-butadiene to form a reaction mixture, and (2) fractionally distilling the reaction mixture to remove a heavier fraction and removing a fraction overhead comprising substantially all of the $C_4$ compounds having reduced acetylenes and 1,2-butadiene content.

12. The process according to claim 11 wherein the hydrogen partial pressure within said distillation column reactor is between 0.1 and 75 psia.

13. The process according to claim 11 wherein the pressure within said distillation column reactor is between 0 and 350 psig.

14. The process according to claim 11 wherein the hydrogen partial pressure within said distillation column reactor is less than 50 psia.

15. The process according to claim 14 wherein the hydrogen partial pressure within said distillation column reactor is less than 35 psia.

16. The process according to claim 11 wherein said acetylenes comprise vinylacetylenes.

17. The process according to claim 11 wherein said acetylenes comprise ethylacetylenes.

* * * * *